US009801947B2

(12) United States Patent
Miller et al.

(10) Patent No.: US 9,801,947 B2
(45) Date of Patent: *Oct. 31, 2017

(54) METHODS AND COMPOSITIONS FOR ENHANCING IMMUNE RESPONSE

(71) Applicant: 3M INNOVATIVE PROPERTIES COMPANY, St. Paul, MN (US)

(72) Inventors: Richard L. Miller, Maplewood, MN (US); Mark A. Tomai, Woodbury, MN (US); Ross M. Kedl, Centennial, CO (US); Isidro Angelo Eleazar Zarraga, Oakland, CA (US); Ronnie Ortiz, Apple Valley, MN (US); James D. Stoesz, Inver Grove Heights, MN (US); Paul D. Wightman, Louisville, KY (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 24 days.

This patent is subject to a terminal disclaimer.

(21) Appl. No.: 14/507,139

(22) Filed: Oct. 6, 2014

(65) Prior Publication Data

US 2015/0044279 A1    Feb. 12, 2015

Related U.S. Application Data

(63) Continuation of application No. 10/821,330, filed on Apr. 9, 2004, now abandoned, which is a continuation-in-part of application No. 10/640,904, filed on Aug. 14, 2003, now Pat. No. 7,427,629.

(60) Provisional application No. 60/545,424, filed on Feb. 18, 2004, provisional application No. 60/545,542, filed on Feb. 18, 2004, provisional application No. 60/533,703, filed on Dec. 31, 2003, provisional application No. 60/515,604, filed on Oct. 30, 2003, provisional application No. 60/515,256, filed on Oct. 29, 2003, provisional application No. 60/462,140, filed on Apr. 10, 2003.

(51) Int. Cl.
A61K 47/48 (2006.01)
A61K 39/39 (2006.01)
A61K 39/00 (2006.01)
A61K 31/44 (2006.01)

(52) U.S. Cl.
CPC ........ *A61K 47/48046* (2013.01); *A61K 31/44* (2013.01); *A61K 39/00* (2013.01); *A61K 39/39* (2013.01)

(58) Field of Classification Search
None
See application file for complete search history.

(56) References Cited

U.S. PATENT DOCUMENTS

| | | |
|---|---|---|
| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gerster |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,525,612 A | 6/1996 | Gerster |
| 5,573,781 A | 11/1996 | Brown et al. |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,741,908 A | 4/1998 | Gerster et al. |
| 5,756,747 A | 5/1998 | Gerster et al. |
| 5,886,006 A | 3/1999 | Nikolaides et al. |
| 5,939,090 A | 8/1999 | Beaurline et al. |

(Continued)

FOREIGN PATENT DOCUMENTS

CN    1377648    11/2002
EP    0 394 026    10/1990

(Continued)

OTHER PUBLICATIONS

Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.

(Continued)

*Primary Examiner* — Frederick Krass
*Assistant Examiner* — Celeste A. Roney
(74) *Attorney, Agent, or Firm* — 3M Innovative Properties Company; Eric E. Silverman

(57) ABSTRACT

Methods and compositions for enhancing the immune response to an IRM compound by depositing within a localized tissue region an IRM depot preparation that provides an extended residence time of active IRM within the localized tissue region.

20 Claims, 1 Drawing Sheet

(56) References Cited

U.S. PATENT DOCUMENTS

| | | |
|---|---|---|
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,113,938 A | 9/2000 | Chen et al. |
| 6,194,425 B1 | 2/2001 | Gerster et al. |
| 6,200,592 B1 | 3/2001 | Tomai et al. |
| 6,245,776 B1 | 6/2001 | Skwierczynski et al. |
| 6,331,539 B1 | 12/2001 | Crooks et al. |
| 6,365,166 B2 | 4/2002 | Beaurline et al. |
| 6,376,669 B1 | 4/2002 | Rice et al. |
| 6,440,992 B1 | 8/2002 | Gerster et al. |
| 6,451,810 B1 | 9/2002 | Coleman et al. |
| 6,486,168 B1 | 11/2002 | Skwierczynski et al. |
| 6,514,985 B1 | 2/2003 | Gerster et al. |
| 6,518,265 B1 | 2/2003 | Kato et al. |
| 6,518,280 B2 | 2/2003 | Gerster |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,610,319 B2 | 8/2003 | Tomai et al. |
| 6,627,638 B2 | 9/2003 | Gerster et al. |
| 6,627,640 B2 | 9/2003 | Gerster et al. |
| 6,630,588 B2 | 10/2003 | Rice et al. |
| 6,638,944 B2 | 10/2003 | Mickelson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,797,718 B2 | 9/2004 | Dellaria et al. |
| 6,800,624 B2 | 10/2004 | Crooks et al. |
| 6,809,203 B2 | 10/2004 | Gerster et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,878,719 B2 | 4/2005 | Lindstrom et al. |
| 6,888,000 B2 | 5/2005 | Crooks et al. |
| 6,894,060 B2 | 5/2005 | Slade |
| 6,897,221 B2 | 5/2005 | Crooks et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,225 B2 | 9/2005 | Lee et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,523 B2 | 7/2006 | Crooks et al. |
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,132,438 B2 | 11/2006 | Frenkel et al. |
| 7,148,232 B2 | 12/2006 | Gerster et al. |
| 7,157,453 B2 | 1/2007 | Crooks et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,301,027 B2 | 11/2007 | Colombo et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,485,432 B2 | 2/2009 | Fink et al. |
| 7,544,697 B2 | 6/2009 | Hays et al. |
| 7,576,068 B2 | 8/2009 | Averett |
| 7,578,170 B2 | 8/2009 | Mayer et al. |
| 7,579,359 B2 | 8/2009 | Krepski et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 7,655,672 B2 | 2/2010 | Statham et al. |
| 7,687,628 B2 | 3/2010 | Gutman et al. |
| 7,696,159 B2 | 4/2010 | Owens et al. |
| 7,699,057 B2 | 4/2010 | Miller et al. |
| 7,731,967 B2 | 6/2010 | O'Hagan et al. |
| 7,799,800 B2 | 9/2010 | Wightman |
| 7,879,849 B2 | 2/2011 | Hays et al. |
| 7,884,207 B2 | 2/2011 | Stoermer et al. |
| 7,888,349 B2 | 2/2011 | Kshirsagar et al. |
| 7,897,597 B2 | 3/2011 | Lindstrom et al. |
| 7,897,609 B2 | 3/2011 | Niwas et al. |
| 7,897,767 B2 | 3/2011 | Kshirsagar et al. |
| 7,902,209 B2 | 3/2011 | Statham et al. |
| 7,902,210 B2 | 3/2011 | Statham et al. |
| 7,902,211 B2 | 3/2011 | Statham et al. |
| 7,902,212 B2 | 3/2011 | Statham et al. |
| 7,902,213 B2 | 3/2011 | Statham et al. |
| 7,902,214 B2 | 3/2011 | Statham et al. |
| 7,902,215 B2 | 3/2011 | Statham et al. |
| 7,902,216 B2 | 3/2011 | Statham et al. |
| 7,902,242 B2 | 3/2011 | Statham et al. |
| 7,902,243 B2 | 3/2011 | Statham et al. |
| 7,902,244 B2 | 3/2011 | Statham et al. |
| 7,902,245 B2 | 3/2011 | Statham et al. |
| 7,902,246 B2 | 3/2011 | Statham et al. |
| 7,906,506 B2 | 3/2011 | Griesgraber et al. |
| 7,915,281 B2 | 3/2011 | Moser et al. |
| 7,939,526 B2 | 5/2011 | Radmer et al. |
| 7,943,609 B2 | 5/2011 | Griesgraber et al. |
| 7,968,562 B2 | 6/2011 | Skwierczynski et al. |
| 7,968,563 B2 | 6/2011 | Kshirsagar et al. |
| 7,993,659 B2 | 8/2011 | Noelle et al. |
| 8,017,779 B2 | 9/2011 | Merrill et al. |
| 8,026,366 B2 | 9/2011 | Prince et al. |
| 8,034,938 B2 | 10/2011 | Griesgraber et al. |
| 2002/0016562 A1* | 2/2002 | Cormier et al. ............... 604/20 |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2003/0118649 A1* | 6/2003 | Gao et al. ............... 424/471 |
| 2003/0133913 A1 | 7/2003 | Tomai et al. |
| 2003/0139364 A1* | 7/2003 | Krieg et al. ............... 514/44 |
| 2004/0014779 A1 | 1/2004 | Gorden et al. |
| 2004/0132079 A1 | 7/2004 | Gupta et al. |
| 2004/0175336 A1 | 9/2004 | Egging et al. |
| 2004/0180919 A1 | 9/2004 | Lee et al. |
| 2004/0191833 A1 | 9/2004 | Fink et al. |
| 2004/0197865 A1 | 10/2004 | Gupta et al. |
| 2004/0202720 A1 | 10/2004 | Wightman et al. |

(56) References Cited

U.S. PATENT DOCUMENTS

| | | |
|---|---|---|
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0048072 A1 | 3/2005 | Kedl et al. |
| 2005/0059072 A1 | 3/2005 | Birmachu et al. |
| 2005/0070460 A1 | 3/2005 | Hammerbeck et al. |
| 2005/0096259 A1 | 5/2005 | Tomai et al. |
| 2005/0106300 A1 | 5/2005 | Chen et al. |
| 2005/0158325 A1 | 7/2005 | Hammerbeck et al. |
| 2005/0165043 A1 | 7/2005 | Miller et al. |
| 2005/0171072 A1 | 8/2005 | Tomai et al. |
| 2005/0239735 A1 | 10/2005 | Miller et al. |
| 2005/0245562 A1 | 11/2005 | Garcia-Echeverria et al. |
| 2006/0045885 A1 | 3/2006 | Kedl et al. |
| 2006/0045886 A1 | 3/2006 | Kedl |
| 2006/0051374 A1 | 3/2006 | Miller et al. |
| 2006/0088542 A1 | 4/2006 | Braun |
| 2006/0142202 A1 | 6/2006 | Alkan et al. |
| 2006/0142235 A1 | 6/2006 | Miller et al. |
| 2006/0195067 A1 | 8/2006 | Wolter et al. |
| 2006/0216333 A1 | 9/2006 | Miller et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0123559 A1 | 5/2007 | Statham et al. |
| 2007/0166384 A1 | 7/2007 | Zarraga et al. |
| 2007/0167479 A1 | 7/2007 | Busch et al. |
| 2007/0213355 A1 | 9/2007 | Capraro et al. |
| 2007/0219196 A1 | 9/2007 | Krepski et al. |
| 2007/0243215 A1 | 10/2007 | Miller et al. |
| 2007/0259881 A1 | 11/2007 | Dellaria et al. |
| 2007/0259907 A1 | 11/2007 | Prince |
| 2007/0292456 A1 | 12/2007 | Hammerbeck et al. |
| 2008/0015184 A1 | 1/2008 | Kshirsagar et al. |
| 2008/0039533 A1 | 2/2008 | Sahouani et al. |
| 2008/0063714 A1 | 3/2008 | Sahouani et al. |
| 2008/0119508 A1 | 5/2008 | Slade et al. |
| 2008/0188513 A1 | 8/2008 | Skwierczynski et al. |
| 2008/0193468 A1 | 8/2008 | Levy et al. |
| 2008/0193474 A1 | 8/2008 | Griesgraber et al. |
| 2008/0207674 A1 | 8/2008 | Stoesz et al. |
| 2008/0213308 A1 | 9/2008 | Valiante et al. |
| 2008/0262021 A1 | 10/2008 | Capraro et al. |
| 2008/0262022 A1 | 10/2008 | Lee et al. |
| 2008/0306252 A1 | 12/2008 | Crooks et al. |
| 2008/0306266 A1 | 12/2008 | Martin et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0023720 A1 | 1/2009 | Kshirsagar et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0035323 A1 | 2/2009 | Stoermer et al. |
| 2009/0062272 A1 | 3/2009 | Bonk et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0124652 A1 | 5/2009 | Ach et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0202443 A1 | 8/2009 | Miller et al. |
| 2009/0221551 A1 | 9/2009 | Kshirsagar et al. |
| 2009/0221556 A1 | 9/2009 | Kshirsagar et al. |
| 2009/0240055 A1 | 9/2009 | Krepski et al. |
| 2009/0246174 A1 | 10/2009 | Rook et al. |
| 2009/0253695 A1 | 10/2009 | Kshirsagar et al. |
| 2009/0270443 A1 | 10/2009 | Stoermer et al. |
| 2009/0298821 A1 | 12/2009 | Kshirsagar et al. |
| 2009/0306388 A1 | 12/2009 | Zimmerman et al. |
| 2010/0028381 A1 | 2/2010 | Gorski et al. |
| 2010/0056557 A1 | 3/2010 | Benninghoff et al. |
| 2010/0096287 A1 | 4/2010 | Stoesz et al. |
| 2010/0113565 A1 | 5/2010 | Gorden et al. |
| 2010/0152230 A1 | 6/2010 | Dellaria et al. |
| 2010/0158928 A1 | 6/2010 | Stoermer et al. |
| 2010/0173906 A1 | 7/2010 | Griesgraber |
| 2010/0180902 A1 | 7/2010 | Miller et al. |
| 2010/0240693 A1 | 9/2010 | Lundquist et al. |
| 2011/0021554 A1 | 1/2011 | Stoesz et al. |

FOREIGN PATENT DOCUMENTS

| | | | |
|---|---|---|---|
| EP | 1 104 764 | | 6/2001 |
| JP | 9-176116 | | 7/1997 |
| JP | 9-208584 | | 8/1997 |
| JP | 11-080156 | | 3/1999 |
| JP | 11-222432 | | 8/1999 |
| JP | 2000-247884 | | 9/2000 |
| WO | WO-96-29394 | * | 9/1996 |
| WO | WO 96/29394 | | 9/1996 |
| WO | WO 00/40228 | | 7/2000 |
| WO | WO-01-10313 | * | 2/2001 |
| WO | WO-01-12158 | * | 2/2001 |
| WO | WO 02/36592 | | 5/2002 |
| WO | WO-2004-032829 | * | 4/2004 |
| WO | WO 2005/003064 | | 1/2005 |
| WO | WO 2006/028451 | | 3/2006 |
| WO | WO 2006/063072 | | 6/2006 |
| WO | WO 2006/121528 | | 11/2006 |
| WO | WO 2007/030775 | | 3/2007 |

OTHER PUBLICATIONS

Brennan et al., "Automated Bioassay of Interferons in Micro-test Plates.", *Biotechniques*, June/July, 78, 1983.

Testerman et al., "Cytokine Induction by the Immunomodulators Imiquimod and S-27609.", *Journal of Leukocyte Biology*, vol. 58, pp. 365-372, Sep. 1995.

Bachman et al., "Synthesis of Substituted Quinolylamines. Derivatives of 4-Amino-7-Chloroquinoline.", *J. Org. Chem.* 15, pp. 1278-1284 (1950).

Jain et al., "Chemical and Pharmacological Investigations of Some ω-Substituted Alkylamino-3-aminopyridines.", *J. Med. Chem.*, 11, pp. 87-92 (1968).

Baranov et al., "Pyrazoles, Imidazoles, and Other 5-Membered Rings.", (1976). *Chem. Abs.* 85, 94362, (1976).

Berényi et al., "Ring Transformation of Condensed Dihydro-astriazines.", *J. Heterocyclic Chem.*, 18, pp. 1537-1540 (1981).

Chollet et al., "Development of a Topically Active Imiquimod Formulation.", *Pharmaceutical Development and Technology*, 4(1), pp. 35-43 (1999).

Izumi et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines.", *Bioorganic & Medicinal Chemistry*, 11, pp. 2541-2550 (2003).

Gerster et al. "Synthesis and Structure" *J. Med Chem.* 2005, 48, 3481-3491.

Lambert. 2000. *European Journal of Pharmaceutical Sciences.* 11(Suppl.2):S15-S27. "Rationale and applications of lipids as prodrug carriers".

Wang. 2003. *Chinese Journal of Pharmaceuticals.* 34(2):73-75. "Comparison of Transdermal Diffusion in vitro of Imiquimod in Liposomes and Cream".

* cited by examiner

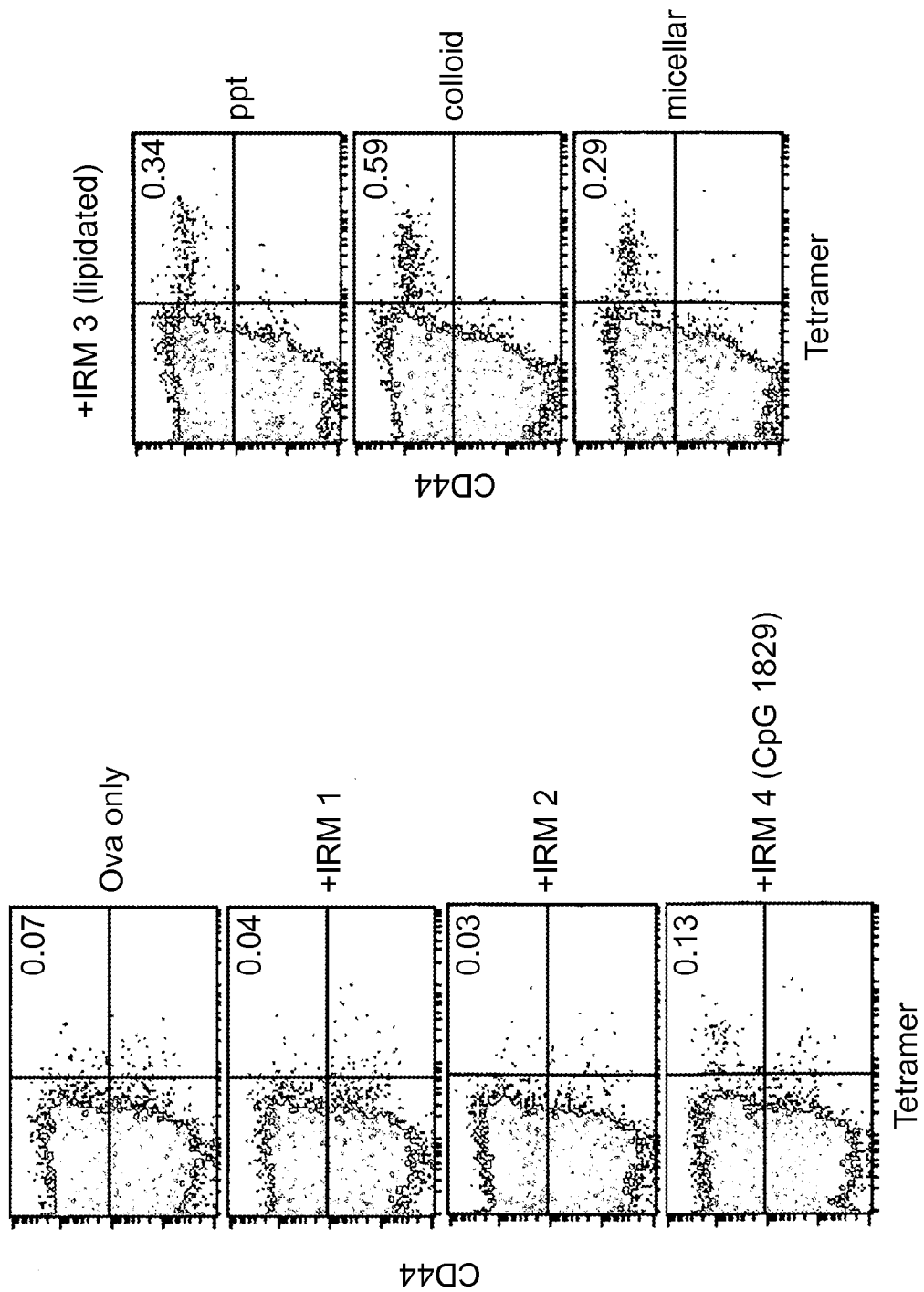

METHODS AND COMPOSITIONS FOR ENHANCING IMMUNE RESPONSE

CROSS-REFERENCE TO RELATED APPLICATIONS

The present application is a Continuation of U.S. patent application Ser. No. 10/821,330, filed on Apr. 9, 2004, which is a Continuation-In-Part of U.S. patent application Ser. No. 10/640,904, filed on Aug. 14, 2003, now U.S. Pat. No. 7,427,629, and claims priority to U.S. Provisional Patent Application Ser. No. 60/533,703, filed Dec. 31, 2003, 60/462,140, filed on Apr. 10, 2003, 60/545,424, filed on Feb. 18, 2004, 60/515,256, filed on Oct. 29, 2003, 60/545,542, filed on Feb. 18, 2004, and U.S. 60/515,604, filed Oct. 30, 2003 each of which is incorporated herein by reference in their entirety.

BACKGROUND

There has been a major effort in recent years, with significant successes, to discover new drug compounds that act by stimulating certain key aspects of the immune system, as well as by suppressing certain other aspects (see, e.g., U.S. Pat. Nos. 6,039,969 and 6,200,592). These compounds, sometimes referred to as immune response modifiers (IRMs), appear to act through basic immune system mechanisms known as toll-like receptors to induce selected cytokine biosynthesis and may be used to treat a wide variety of diseases and conditions. For example, certain IRMs may be useful for treating viral diseases (e.g., human papilloma virus, hepatitis, herpes), neoplasias (e.g., basal cell carcinoma, squamous cell carcinoma, actinic keratosis), and TH2-mediated diseases (e.g., asthma, allergic rhinitis, atopic dermatitis), and are also useful as vaccine adjuvants. Unlike many conventional anti-viral or anti-tumor compounds, the primary mechanism of action for IRMs is indirect, by stimulating the immune system to recognize and take appropriate action against a pathogen.

Many of the IRM compounds are small organic molecule imidazoquinoline amine derivatives (see, e.g., U.S. Pat. No. 4,689,338), but a number of other compound classes are now known as well (see, e.g., U.S. Pat. No. 5,446,153) and more are still being discovered. Other IRMs have higher molecular weights, such as oligonucleotides, including CpGs (see, e.g., U.S. Pat. No. 6,194,388). In view of the great therapeutic potential for IRMs, and despite the important work that has already been done, there is a substantial ongoing need for new means of controlling the delivery and activity of IRMs in order to expand their uses and therapeutic benefits.

SUMMARY

It has been found that many immune response modifier (IRM) compounds (described infra) often have a relatively short half-life in terms of residence time at a given delivery location, typically less than about 1-2 hours for small molecule IRMs. They appear to be cleared, metabolized, or simply diffuse away from within a local delivery site rather easily in many cases. This short residence duration may reduce the IRM's ability to activate some immune system cells at the desired site. Hence, it is now believed that the effectiveness of IRM compounds may be enhanced by maintaining a depot of active IRM compound within a localized region of tissue for an extended period. Importantly, not only do IRMs have the ability to modulate the immune system locally, but by inducing certain chemokines, such as, e.g., MIP-3α, MIP-1α, IP-10, they can recruit additional critical immune system cells, such as dendritic cells, to the localized tissue region. For example, Furumoto et al., *J Clin Invest*, March 2004, no. 113(5):774-83, discusses the use of CCL20/MIP-3alpha and CpGs to recruit dendritic cells, although apparently not in a depot. But by maintaining the IRM present for an extended period within the localized tissue region, the IRM can further activate the immune system cells that have been recruited to the localized site, thus creating a further synergistic effect.

The IRM depoting methods and compositions of the present invention can thus provide important additional time for activation and/or infiltration of responsive immune system cells (e.g., dendritic cells, monocytes/macrophages, and B cells) within a specific localized tissue region. Moreover, these methods and formulations may also help assure that the immune response is correctly targeted to an immunogen at the intended desired tissue location (e.g., where there are neoplastic cells, virus infected cells, or vaccine antigen present). This later point—the ability to target by co-locating the IRM, antigen presenting cells (APCs), and antigen—is surprisingly important because it may enhance recognition by the immune system of the targeted disease antigens, and may also reduce the potential for unwanted immune system stimulation away from the actual disease target.

It is also believed that IRM depot preparations that provide a pulsed IRM delivery (i.e., where the active IRM is release intermittently in pulses over time) may be particularly desirable for certain applications.

Accordingly, the invention includes a method of enhancing the immune response to an IRM compound, comprising depositing within a localized tissue region an IRM depot preparation that provides an extended residence time within the localized tissue region. This contrasts with either injection of a simple solution or topical delivery via cream, gel, or patch. The invention also includes IRM depot preparations disclosed herein, and methods of treatment using the IRM depot preparations disclosed herein.

The IRM localized tissue region may be, e.g., a cancer, infected lesion or organ, or vaccination site. The localized tissue region may be, e.g., a breast cancer tumor, stomach cancer tumor, lung cancer tumor, head or neck cancer tumor, colorectal cancer tumor, renal cell carcinoma tumor, pancreatic cancer tumor, basal cell carcinoma tumor, pancreatic cancer tumor, cervical cancer tumor, melanoma cancer tumor, prostate cancer tumor, ovarian cancer tumor, or bladder cancer tumor. The localized tissue region may include a vaccine.

The IRM depot preparation may comprise, e.g., a lipid-modified IRM, an IRM compound attached to support material, solid particles of IRM compound, an emulsion, micelles, an IRM within a biodegradable polymer matrix, IRM compound incorporated into lipid membranes, lipid vesicles, or liposomes.

The IRM depot preparation may provide pulsed delivery of an IRM compound to the localized tissue region. The IRM depot preparation may comprise an osmotically driven cylinder. The IRM depot preparation may be delivered within the localized tissue region using, e.g., needle injection, surgical implantation, laparoscopic implantation, catheter implantation, a microneedle array, or high-velocity particle implantation.

The IRM may be an agonist of at least one TLR selected from the group consisting of TLR6, TLR7, TLR8, TLR9 and combinations thereof. The IRM may be a selective TLR agonist of TLR 7, TLR 8, or TLR 9, or an agonist of both TLR 7 and 8. Many of the IRM compounds disclosed herein are TLR 7 and/or 8 agonists. The IRM may alternatively be a TLR 4 agonist. The IRM may be preferably be a small molecule immune response modifier, for example comprising a 2-aminopyridine fused to a five membered nitrogen-containing heterocyclic ring.

The term "comprises" and variations thereof do not have a limiting meaning where these terms appear in the description and claims.

As used herein, "a," "an," "the," "at least one," and "one or more" are used interchangeably.

As used herein, "treating" a condition or a subject includes therapeutic, prophylactic, and diagnostic treatments.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used individually and in various combinations. In each instance, the recited list serves only as a representative group and should not be interpreted as an exclusive list.

Various other features and advantages of the present invention should become readily apparent with reference to the following detailed description, examples, claims and appended drawings. In several places throughout the specification, guidance is provided through lists of examples. In each instance, the recited list serves only as a representative group and should not be interpreted as an exclusive list.

BRIEF DESCRIPTION OF THE DRAWINGS

FIG. 1 shows flow cytometry data for the Example.

DETAILED DESCRIPTION OF ILLUSTRATIVE EMBODIMENTS OF THE INVENTION

The present invention is directed to methods and formulations of immune response modifiers (IRMs) that can be deposited within a localized tissue region and provide locally active IRM compounds for an extended period of time. One way this can be described is in terms of the IRM half-life within a localized tissue region. To illustrate, if a conventional solution formulation of a given IRM compound is injected into a solid tumor so as to achieve a resulting tissue concentration of active IRM within the tumor, the concentration may be about half only two hours later. This would be considered an IRM residence half-life of about 2 hours, although the rate of IRM clearance may not always be constant. By contrast, if an IRM depot preparation such as those described herein is injected into a localized tissue region, such as solid tumor, so as to achieve a desired IRM concentration, the concentration of active IRM in the tumor tissue (localized tissue region) may not be down to half until, e.g., 10-14 days later. This would be considered an IRM residence half-life of about 2 weeks.

The present invention thus provides active IRMs within a localized tissue region for a time longer than a comparable concentration of the IRM in a conventional solution, wherein at least about 50% of the IRM compound delivered via the IRM depot preparation remains localized at the treatment site for more than at least about 2 hours. For example, the IRM residence half-life may be at least 12 hours, 24 hours, 7 days, two weeks, a month, or even several months.

As described below, the benefits of the present invention in terms of enhanced immune response and/or better targeting of the immune system to intended antigens can be accomplished with many different IRM depot preparations, IRM compounds, optionally with other active agents, and can be delivered to various localized tissue regions for a wide range of treatments.

IRM Depot Preparations

As used herein, IRM depot preparation refers to compositions that provide active IRM compound for an extended period to a localized tissue region (as opposed to an extended release IRM formulation for providing extended systemic delivery, although that may use a drug depot for systemic delivery).

There are at least two general ways of maintaining a localized IRM depot effect. The IRM may either be attached to some other material that helps hold the IRM in place within the desired localized tissue region, or the IRM may be released over time from a controlled release formulation in such a way that active IRM is present locally at a desired concentration for an extended period.

Examples of attaching an IRM to another material that can be used in an IRM depot preparation include the IRM-support complexes disclosed in, e.g., copending applications U.S. 60/462,140, 60/515256, and US 2003/25523.

Examples of controlled release formulations and methods that can be used in an IRM depot preparation, although typically used for extended release systemic drug delivery, are disclosed in, e.g., U.S. Pat. No. 6,126,919 (biocompatible compounds), O'Hagan and Singh, Microparticles as vaccine adjuvants and delivery systems, *Expert Rev. Vaccines* 2(2), p. 269-83 (2003), and Vogel et al., *A Compendium of Vaccine Adjuvants and Excipients*, $2^{nd}$ Edition, Bethesda, Md.: National Institute of Allergy & Infectious Diseases, 1998 (available at www.niaid.nih.gov/hivvaccines/pdf/compendium.pdf). Also, it is usually desired to prevent, or at least reduce the occurrence of, the systemic distribution of the IRM after it leaves the localized tissue region. One way to facilitate this is to select an IRM that is metabolized or cleared rapidly once the IRM leaves the localized tissue region.

Some general examples of IRM depot preparations that can provide an increased IRM residence time within a localized tissue region include but are not limited to the following:

1. The IRM compound may be attached (e.g., conjugated, coated, or ion-paired) onto to other support materials, such as plastic, metal, minerals (e.g., alum), or silicone, in the form of particles, beads, fibers, meshes, polymers, etc., as disclosed in, e.g., copending applications U.S. 60/462,140, 60/515256, and US 2003/25523. These IRM support complexes can then be deposited within a desired tissue site and remain in place and active for an extended period of time. This a highly versatile approach in part because the IRM compounds can be attached to many different support complex materials, and because the IRM can remain active even while they remain attached to the support complex material.

For example, IRM, and an antigen if desired, may adsorb onto the surface of alum particles to enhance antigen presentation and endocytosis of particulates. Another example would where the IRM is covalently linked to a polymer backbone through a link that is subject to hydrolysis or enzymatic activity at a slow, controlled rate.

2. The IRM compound may be conjugated directly to a lipid group, as disclosed in, e.g., copending application U.S. 60/515,604, which in itself can provide an IRM depot preparation. These lipid-modified or lipidated IRMs may also be used as the IRM compound in the other IRM depot preparations described herein, e.g., for formation of suspensions, incorporation into emulsions, lipid membranes, lipid vesicles, liposomes, and the like.

For example, if a lipidated IRM is in suspension, formulations of which are described below, is injected subcutaneously at 10 mg/kg (200 ug of drug in a normal B6 mouse), a substantial amount of the IRM depot preparation is still visible under the skin 10-14 days later.

3. The IRM compound may be used in the form of solid IRM particles, where the particles may have a limited solubility so that once implanted within the localized tissue region they dissolve slowly over an extended period. This contrasts with the situation where solid drug particle suspensions are delivered that then dissolve relatively quickly upon delivery (e.g., within an hour). The IRM particles may be amorphous or crystalline and in the form of fine powders, liquid suspensions, such as colloidal suspensions, or may be included within gels or creams, and the like. The solid IRM particles may be essentially pure IRM compound, or may include carriers or fillers. The average size of the particles may be less than 1 micron, or from about 1-100 microns, or larger than 100 microns, depending on the particular IRM used and the desired release characteristics. An average particle size of between 1-20 microns will often be suitable. When introduced within a localized tissue region the solid IRM particles can slowly release active IRM compound the local area, providing extended residence times. The rate of release will depend on solubility of the particular IRM used, which may be influenced by such things as selection of polymorph forms, salts, and stereoisomers, in addition to the physicochemical properties of any carriers or fillers, if used.

For example, a colloidal IRM suspension may be formed using an IRM dissolved in a water-miscible organic injectable solvent (e.g. N-methyl pyrrolidone or NMP) (compartment 1). Then, an antigen, if desired, may be dissolved in an aqueous solution with surfactants (e.g. Tween 80) (compartment 2). Prior to administration to a localized tissue region, such as subcutaneous injection, colloidal particles of IRM are formed by mixing compartment 1 into compartment 2, causing precipitation of IRM into fine particles. Of course, where appropriate an IRM colloidal suspension can be made prior to packaging, with instructions for shaking/vortexing prior to administration.

4. The IRM compound may be encapsulated, incorporated, or dissolved into biodegradable polymeric matrices such as poly lactic acid (polylactides), poly glycolic acid (polyglycolides), poly(d,l-lactide-co-glycolide) (PLGA), polyorthoesters, polyanhydrides, polyphosphazenes, and polyurethanes. Such biodegradable matrices are often used to provide extended release systemic drug delivery, but can also be adapted for use to provide extended IRM delivery within a localized tissue region, for example directly within a tumor mass, infection site, or vaccination site.

For example, an IRM compound and a vaccine antigen may be dissolved in a polymer solvent like N-methyl pyrrolidone or NMP (compartment 1). A selected polymer may then be dissolved in the solvent (compartment 2). Compartment 1 and 2 are mixed upon administration, e.g., using a double cartridge syringe with a static mixer. When injected, the solvent (e.g. NMP) which is miscible with water, diffuses away, leaving a semi-solid implant containing both IRM and Antigen.

5. The IRM compound may be incorporated into single emulsions such as oil-in-water (o/w) or water-in-oil (w/o), or multiple emulsions such as water-in-oil-in water (w/o/w) and oil-in-water-in-oil (o/w/o). Antigen can also be incorporated into the emulsion in addition to the IRM (e.g. to generate a more specific immune response). The IRM and antigen can partition between the oil and water phases, or lie on the discrete phase (e.g. oil droplet) surface. The emulsion format may act synergistically with the IRM for improved immune response (e.g. antigen on oil droplet surface may enhance its presentation to cells of the immune system, while IRM can enhance uptake of the antigen on the oil droplet by cells of the immune system.

For example, an o/w emulsion may use an IRM in a MF59-based emulsion containing squalene (oil-phase) and surfactant (e.g., Tween 80, Span 85), and water. The IRM may be pre-dissolved in the water phase or the oil phase. Another example is to use a vegetable oil (sesame oil, soybean oil, mineral oil, e.g. emulsion based on Freund's Incomplete Adjuvant, etc.) with IRM and surfactant (e.g., lecithin) in water. A w/o emulsion may use an IRM dissolved in water, surfactant (e.g., mannide monooleate) and mineral oil. A w/o emulsion can also be made using water with IRM dissolved, and injectable vegetable oils with appropriate emulsifiers and surfactants (Tween 80, Cremophore EL, etc.). Antigen may also be pre-dissolved in water or the oil phase and incorporated in the emulsion.

6. The IRM compound may be incorporated into lipid membranes, lipid vesicles, and liposomes. Within lipsome preparations, the IRM may be loaded into the membrane, on the membrane surface, or in the liposome core. For example, IRM liposomes may use DOTAP transfection agent and cholesterol to entrap IRM, and antigen if desired, in a liposome.

7. The IRM compound may be delivered to the localized tissue region using an osmotically driven cylinder implanted within the tissue.

8. The IRM compound may be incorporated into a bioadhesive polymer such as a hydrogel, including, for example, those described by H. S. Sawhney, C. P. Pathak and J. A. Hubell in Macromolecules, (1993) 26:581-587, as well as polyhyaluronic acids, casein, polysaccharides, keratin, collagen, gelatin, glutin, polyethylene glycol, crosslinked albumin, fibrin, polyanhydrides, polyacrylic acids, alginate, chitosan, poly(methyl methacrylates), poly(ethyl methacrylates), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), and cellulose gums. Alternatively, polymeric hydrogel materials can be constructed from poly(vinyl alcohol) precursors as disclosed in U.S. Pat. Nos. 4,528,325 and 4,618,649 or from poly(methyl methacrylate). Poly(methyl methacrylate) is commercially available and is often used in ophthalmic devices such as intraocular lenses, contact lenses, and the like.

A suitable hydrogel can be natural, synthetic, or a combination thereof. In some embodiments, the hydrogel can be thermally responsive to a designed temperature such as, for example, a hydrogel as described in U.S. patent application Ser. No. 10/626,261, filed Jul. 24, 2003. For example, the thermally responsive hydrogels can be harden when they are warmed up to body temperature, can be further harden upon UV irradiation.

Bioadhesive organic polymers are preferred for certain applications of IRMs. For example, if the IRM is to be used for treating bladder cancer, a bioadhesive polymer may be desired. Advantageously, the adhesive qualities of the formulation would allow the IRM to be in contact with the biological tissue allowing for greater contact time for cytokine induction.

It should also be noted that where solid particles are involved, the particles may be in any number of forms, e.g., irregular particulates, spheres, plates, flakes, rods or other shapes, and they may be porous or non-porous. Particles can be lyophilized, then for example provided with a diluent to create a microsuspension prior to administration. For vaccines, antigen may be encapsulated within a particle matrix, for example a biodegradable polymer, and IRM compound either incorporated into or adsorbed on surface of the particle, either by physical or chemical adsorption.

The IRM depot preparations may provide IRM compound to the desired localized tissue region with various IRM residence half-life times, generally of at least 2 hours. For example, the IRM residence half-life may be at least 12 hours, 24 hours, 7 days, two weeks, a month, or even several months.

Further, the IRM depot preparation can be designed to achieve constant or pulsed delivery to the localized tissue region. Pulsed delivery may be desirable in order to provide intermittent dosing of an IRM to the local tissue region over time. For example, a combination of biodegradable polymers can be used that have differing degradation, and thus IRM release, rates. The depot preparation may contain a homogeneous mixture of various biodegradable polymers, or the polymers may be utilized in a segmented fashion to achieve complex degradation profiles. The depot preparation may also be coated with various polymers to achieve zero-order, first-order, and pulsatile IRM release. If in the form of particles, some particles may use a polymer matrix that releases the IRM (and other optional ingredients, such as vaccine antigen) over 24 hours, other particles that release about two weeks later, and so on. It may be particularly desirable for vaccine purposes to provide continuous release of an antigen and use an IRM depot preparation that provides pulsatile release of the IRM compound. Also, the IRM release timing may either be regular, e.g., initially and once weekly for several weeks, or it may be irregular, e.g., initially and then 3 days, 2 weeks, and 2 months apart.

The IRM depot preparations may be delivered into a desired localized tissue region via any suitable route, e.g., including but not limited to a subcutaneous, intradermal, intramuscular, intrathecal, intra-organ, intratumoral, intralesional, intravesicle, and intraperitoneal route of delivery. A "localized tissue region" will generally be a relatively small portion of the body, e.g., less than 10% by volume, and often less than 1% by volume. For example, depending on the size of, e.g., a solid tumor or cancerous organ, the localized tissue region will typically be on the order of no more than about 500 $cm^3$, often less than about 100 $cm^3$, and in many instances 10 $cm^3$ or less. For some applications the localized tissue region will be 1 $cm^3$ or less (e.g., for small tumor nodules, viral lesions, or vaccination sites). However, in certain instances the localized tissue region may be a particularly large region, up to several liters, for example to treat metastasized cancer within the entire peritoneal cavity (e.g., using an IRM depot preparation to retain the IRM for an extended time within the peritoneal cavity). The IRM depot preparations may be delivered using, e.g., needle injection, surgical, laparoscopic, or catheter implantation, microneedle array, high-velocity particle implantation, or any other known method for introducing a preparation into a localized tissue region. Delivery to the localized tissue region may be in conjunction with image guiding techniques using, for example, ultrasound, MRI, real-time X-ray (fluoroscopy), etc.

Additional Agents

In addition to one or more IRM compounds, the IRM depot preparations and methods of the present invention can include additional agents. Alternatively, the additional agent(s) can be administered separately from the IRM depot preparation.

Such additional agents may be additional drugs, including, for example, a vaccine or a tumor necrosis factor receptor (TNFR) agonist. Vaccines include any material that raises either humoral and/or cell mediated immune response, such as live or attenuated viral and bacterial immunogens and inactivated viral, tumor-derived, protozoal, organism-derived, fungal, and bacterial immunogens, toxoids, toxins, polysaccharides, proteins, glycoproteins, peptides, cellular vaccines, such as using dendritic cells, DNA vaccines, recombinant proteins, glycoproteins, and peptides, and the like, for use in connection with, e.g., cancer vaccines, BCG, cholera, plague, typhoid, hepatitis A, B, and C, influenza A and B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, severe acute respiratory syndrome (SARS), anthrax, and yellow fever. See also, e.g., vaccines disclosed in WO 02/24225. Such additional agents can include, but are not limited to, drugs, such as antiviral agents or cytokines. The vaccine may be separate or may be physically or chemically linked to the IRM, such as by chemical conjugation or other means, so that they are delivered as a unit. TNFR agonists that may be delivered in conjunction with the IRM depot preparation include, but are not limited to, CD40 receptor agonists, such as disclosed in copending application U.S. 60/437,398. Other active ingredients for use in combination with an IRM depot preparation of the present invention include those disclosed in, e.g., US 2003/0139364.

Immune Response Modifier Compounds:

Immune response modifiers ("IRM") useful in the present invention include compounds that act on the immune system by inducing and/or suppressing cytokine biosynthesis. IRM compounds possess potent immunostimulating activity including, but not limited to, antiviral and antitumor activity, and can also down-regulate other aspects of the immune response, for example shifting the immune response away from a TH-2 immune response, which is useful for treating a wide range of TH-2 mediated diseases. IRM compounds can also be used to modulate humoral immunity by stimulating antibody production by B cells. Further, various IRM compounds have been shown to be useful as vaccine adjuvants (see, e.g., U.S. Pat. No. 6,083,505, U.S. Pat. No. 6,406,705, and WO 02/24225).

In particular, certain IRM compounds effect their immunostimulatory activity by inducing the production and secretion of cytokines such as, e.g., Type I interferons, TNF-α, IL-1, IL-6, IL-8, IL-10, IL-12, IP-10, MIP-1, MIP-3, and/or MCP-1, and can also inhibit production and secretion of certain TH-2 cytokines, such as IL-4 and IL-5. Some IRM compounds are said to suppress IL-1 and TNF (U.S. Pat. No. 6,518,265).

For some embodiments, the preferred IRM compounds are so-called small molecule IRMs, which are relatively small organic compounds (e.g., molecular weight under about 1000 daltons, preferably under about 500 daltons, as opposed to large biologic protein, peptides, and the like). Although not bound by any single theory of activity, some IRMs are known to be agonists of at least one Toll-like receptor (TLR). IRM compounds that are agonists for TLRs selected from 6, 7, 8, and/or 9 may be particularly useful for certain applications. In some applications, for example, the preferred IRM compound is not a TLR7 agonist and is a TLR8 or TLR9 agonist. In other applications, for example, the IRM is a TLR7 agonist and is not a TLR 8 agonist. Some small molecule IRM compounds are agonists of TLRs such as 6, 7, and/or 8, while oligonucleotide IRM compounds are agonists of TLR9, and perhaps others. Thus, in some embodiments, the IRM that is included in the IRM delivery apparatus may be a compound identified as an agonist of one or more TLRs.

For example, without being bound to any particular theory or mechanism of action, IRM compounds that activate a strong cytotoxic lymphocyte (CTL) response may be particularly desirable as vaccine adjuvants, especially for therapeutic viral and/or cancer vaccines because a therapeutic effect in these settings is dependent on the activation of cellular immunity. For example, studies have shown that activation of T cell immunity in a given patient has a significant positive effect on the prognosis of the patient. Therefore the ability to enhance T cell immunity is believed to be critical to producing a therapeutic effect in these disease settings.

IRM compounds that are TLR 8 agonists may be particularly desirable for use with therapeutic cancer vaccines because antigen presenting cells that express TLR8 have been shown to produce IL-12 upon stimulation through TLR8. IL-12 is believed to play a significant role in activation of CTLs, which are important for mediating therapeutic efficacy as described above.

IRM compounds that are TLR 7 agonists and/or TLR 9 agonists may be particularly desirable for use with prophylactic vaccines because the type I interferon induced by stimulation through these TLRs is believed to contribute to the formation of neutralizing Th1-like humoral and cellular responses.

IRM compounds that are both TLR 7 and TLR 8 agonists may be particularly desirable for use with therapeutic viral vaccines and/or cancer vaccines because TLR7 stimulation is believed to induce the production of type I IFN and activation of innate cells such as macrophages and NK cells, and TLR8 stimulation is believed to activate antigen presenting cells to initiate cellular adaptive immunity as described above. These cell types are able to mediate viral clearance and/or therapeutic growth inhibitory effects against neoplasms.

IRM compounds that are non-TLR 7 agonists, and do not induce substantial amounts of interferon alpha, may be desirable for use with certain vaccines such as bacterial vaccines because TLR7 induces type I IFN production, which down-regulates the production of IL-12 from macrophages and DCs. IL-12 contributes to the subsequent activation of macrophages, NK cells and CTLs, all of which contribute to anti-bacterial immunity. Therefore the induction of anti-bacterial immunity against some kinds of bacteria may be enhanced in the absence of IFNa.

For purposes of the present application, one way to determine if an IRM compound is considered to be an agonist for a particular TLR is if it activates an NFkB/luciferase reporter construct through that TLR from the target species more than about 1.5 fold, and usually at least about 2 fold, in TLR transfected host cells such as, e.g., HEK293 or Namalwa cells relative to control transfectants. For information regarding TLR activation, see, e.g., applications WO 03/043573, U.S. 60/447,179, U.S. 60/432,650, U.S. 60/432,651, and U.S. 60/450,484, WO 03/043588 and the other IRM patents and applications disclosed herein.

Preferred IRM compounds include a 2-aminopyridine fused to a five-membered nitrogen-containing heterocyclic ring.

Examples of classes of small molecule IRM compounds include, but are not limited to, derivatives of imidazoquinoline amines including but not limited to amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, and thioether substituted imidazoquinoline amines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including but not limited to amide substituted imidazopyridines, sulfonamido substituted imidazopyridines, and urea substituted imidazopyridines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; and thiazolonaphthyridine amines, such as those disclosed in, for example, U.S. Pat. Nos. 4,689,338; 4,929,624; 4,988,815; 5,037,986; 5,175,296; 5,238,944; 5,266,575; 5,268,376; 5,346,905; 5,352,784; 5,367,076; 5,389,640; 5,395,937; 5,446,153; 5,482,936; 5,693,811; 5,741,908; 5,756,747; 5,939,090; 6,039,969; 6,083,505; 6,110,929; 6,194,425; 6,245,776; 6,331,539; 6,376,669; 6,451,810; 6,525,064; 6,545,016; 6,545,017; 6,558,951; and 6,573,273; European Patent 0 394 026; U.S. Patent Publication No. 2002/0055517; and International Patent Publication Nos. WO 01/74343; WO 02/46188; WO 02/46189; WO 02/46190; WO 02/46191; WO 02/46192; WO 02/46193; WO 02/46749; WO 02/102377; WO 03/020889; WO 03/043572 and WO 03/045391.

Additional examples of small molecule IRMs said to induce interferon (among other things), include purine derivatives (such as those described in U.S. Pat. Nos. 6,376,501, and 6,028,076), imidazoquinoline amide derivatives (such as those described in U.S. Pat. No. 6,069,149), and benzimidazole derivatives (such as those described in U.S. Pat. No. 6,387,938). 1H-imidazopyridine derivatives (such as those described in U.S. Pat. No. 6,518,265) are said to inhibit TNF and IL-1 cytokines Other small molecule IRMs said to be TLR 7 agonists are shown in U.S. 2003/0199461 A1.

Examples of small molecule IRMs that include a 4-aminopyrimidine fused to a five-membered nitrogen-containing heterocyclic ring include adenine derivatives (such as those described in U.S. Pat. Nos. 6,376,501; 6,028,076 and 6,329,381; and in WO 02/08595).

In some applications, for example, the preferred IRM compound is other than imiquimod or S-28463 (i.e., resiquimod: 4-Amino-α,α-dimethyl-1H-imidazo[4,5-c]quinoline-1-ethanol).

Examples of particular IRM compounds include 2-propyl[1,3]thiazolo[4,5-c]quinolin-4-amine, which is considered predominantly a TLR 8 agonist (and not a substantial TLR 7 agonist), 4-amino-α,α-dimethyl-1H-imidazo[4,5-c]quinoline-1-ethanol, which is considered predominantly a TLR 7 agonist (and not a substantial TLR 8 agonist), and 4-amino-2-(ethoxymethyl)-α,α-dimethyl-6,7,8,9-tetrahydro-1H-imidazo[4,5-c]quinoline-1-ethanol, which is a TLR 7 and TLR 8 agonist. In addition to its TLR 7 activity (and TLR 6 activity, but low TLR 8 activity), 4-amino-α,α-dimethyl-1H-imidazo[4,5-c]quinoline-1-ethanol has beneficial characteristics, including that it has a much lower CNS effect when delivered systemically compared to imiquimod. Other examples of specific IRM compounds include, e.g., N-[4-(4-amino-2-butyl-1H-imidazo[4,5-c][1,5]naphthyridin-1-yl)butyl]-N'-cyclohexylurea, 2-methyl-1-(2-methylpropyl)-1H-imidazo[4,5-c][1,5]naphthyridin-4-amine, 1-(2-methylpropyl)-1H-imidazo[4,5-c][1,5]naphthyridin-4-amine, N-{2-[4-amino-2-(ethoxymethyl)-1H-imidazo[4,5-c]quinolin-1-yl]-1,1-dimethylethyl}methanesulfonamide, N-[4-(4-amino-2-ethyl-1H-imidazo[4,5-c]quinolin-1-yl)butyl]methanesulfonamide, 2-methyl-1-[5-(methylsulfonyl)pentyl]-1H-imidazo[4,5-c]quinolin-4-amine, N-[4-(4-amino-2-propyl-1H-imidazo[4,5-c]quinolin-1-yl)butyl]methanesulfonamide, 2-butyl-1-[3-(methylsulfonyl)propyl]-1H-imidazo[4,5-c]quinoline-4-amine, 2-butyl-1-{2-[(1-methylethyl)sulfonyl]ethyl}-1H-imidazo[4,5-c]quinolin-4-amine, N-{2-[4-amino-2-(ethoxymethyl)-1H-imidazo[4,5-c]quinolin-1-yl]-1,1-dimethylethyl}-N'-cyclohexylurea, N-{2-[4-amino-2-(ethoxymethyl)-1H-imidazo[4,5-c]quinolin-1-yl]-1,1-dimethylethyl}cyclohexanecarboxamide, N-{2-[4-amino-2-(ethoxymethyl)-1H-imidazo[4,5-c]quinolin-1-yl]ethyl}-N'-isopropylurea. Resiquimod, 4-amino-2-ethoxymethyl-α,α-dimethyl-1H-imidazo[4,5-c]quinoline-1-ethanol, may also be used in certain situations where a combination TLR 7 and TLR 8 agonist is desired.

Other IRM compounds include large biological molecules such as oligonucleotide sequences. Some IRM oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. CpG7909 is a specific example. Other IRM nucleotide sequences lack CpG and are described, for example, in International Patent Publication No. WO 00/75304. However, the large biological molecule IRMs may be less susceptible to rapid clearance from a localized tissue region and, consequently, the IRM depot preparations described herein may be especially useful in connection with small molecule IRMs described above.

Exemplary Applications:

IRM depot preparations delivered to a localized tissue region can be used in a wide variety of applications, such as in the treatment of a wide variety of conditions. For example, IRMs such as imiquimod—a small molecule, imidazoquinoline IRM, marketed as ALDARA (3M Pharmaceuticals, St. Paul, Minn.)—have been shown to be useful for the therapeutic treatment of warts, as well as certain cancerous or pre-cancerous lesions (See, e.g., Geisse et al., *J. Am. Acad. Dermatol.,* 47(3): 390-398 (2002); Shumack et al., *Arch. Dermatol.,* 138: 1163-1171 (2002); U.S. Pat. No. 5,238,944 and International Publication No. WO 03/045391.

Other diseases for which IRMs identified herein, including as an IRM depot preparation, may be used as treatments include, but are not limited to:

viral diseases, such as genital warts, common warts, plantar warts, hepatitis B, hepatitis C, herpes simplex virus type I and type II, molluscum contagiosum, variola, HIV, CMV, VZV, rhinovirus, adenovirus, coronavirus, influenza, para-influenza;

bacterial diseases, such as tuberculosis, and mycobacterium avium, leprosy;

other infectious diseases, such as fungal diseases, chlamydia, candida, aspergillus, cryptococcal meningitis, pneumocystis carnii, cryptosporidiosis, histoplasmosis, toxoplasmosis, trypanosome infection, leishmaniasis;

neoplastic diseases, such as intraepithelial neoplasias, cervical dysplasia, actinic keratosis, basal cell carcinoma, squamous cell carcinoma, hairy cell leukemia, Karposi's sarcoma, melanoma, renal cell carcinoma, myelogeous leukemia, multiple myeloma, non-Hodgkin's lymphoma, cutaneous T-cell lymphoma, and other cancers;

TH-2 mediated, atopic, and autoimmune diseases, such as atopic dermatitis or eczema, eosinophilia, asthma, allergy, allergic rhinitis, systemic lupus erythematosis, essential thrombocythaemia, multiple sclerosis, Ommen's syndrome, discoid lupus, alopecia areata, inhibition of keloid formation and other types of scarring, and enhancing would healing, including chronic wounds; and as a vaccine adjuvant for use in conjunction with any material that raises either humoral and/or cell mediated immune response, such live viral and bacterial immunogens and inactivated viral, tumor-derived, protozoal, organism-derived, fungal, and bacterial immunogens, toxoids, toxins, polysaccharides, proteins, glycoproteins, peptides, cellular vaccines, DNA vaccines, recombinant proteins, glycoproteins, and peptides, and the like, for use in connection with, e.g., cancers, BCG, cholera, plague, typhoid, hepatitis A, B, and C, influenza A and B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, and yellow fever.

The IRM depot preparations of the invention may be particularly beneficial for use within solid tumors and cancerous organs or tissue regions. If the residence time of the IRM is extended within the cancerous tissue, it is believed that the body's immune response to the cancer can be enhanced and directly targeted to relevant tumor antigens. This not only may help reduce or eliminate cancer at the site of IRM depot preparation delivery, but, by sensitizing the immune system to the cancer, may help the immune system attack the cancer in other locations throughout the body. This approach to treatment may be used alone or in conjunction with other treatments for the cancer, such as therapeutic cancer vaccination (which may further include use of an IRM depot preparation), antibody based therapies such as Rituxan and Herceptin, and other chemotherapies. Examples of cancers that may be particularly suitable for direct injection of an IRM depot preparation into a localized tissue region include, but are not limited to, breast cancer, lung cancer, stomach cancer, head and neck cancer, colorectal cancer, renal cell carcinoma, pancreatic cancer, basal cell carcinoma, cervical cancer, melanoma, prostate cancer, ovarian cancer, and bladder cancer.

The methods, materials, and articles of the present invention may be applicable for any suitable subject. Suitable subjects include, but are not limited to, animals such as, but not limited to, humans, non-human primates, rodents, dogs, cats, horses, pigs, sheep, goats, cows, or birds. IRMs may also be particularly helpful in individuals having compromised immune functioning, such as those with HIV AIDS, transplant patients, and cancer patients.

An amount of an IRM depot preparation effective for a given therapeutic or prophylactic application is an amount sufficient to achieve the intended therapeutic or prophylactic application. The precise amount of IRM depot preparation used will vary according to factors known in the art including but not limited to the physical and chemical nature of the IRM compound, the nature of the composition, the intended dosing regimen, the state of the subject's immune system (e.g., suppressed, compromised, stimulated), the method of administering the IRM compound, and the species to which the formulation is being administered. Accordingly it is not practical to set forth generally the amount that constitutes an amount of IRM and IRM depot preparation effective for all possible applications. Those of ordinary skill in the art, however, can readily determine an appropriate amount with due consideration of such factors.

EXAMPLE

The following example has been selected merely to further illustrate features, advantages, and other details of the invention. It is to be expressly understood, however, that while the example serve this purpose, the particular materials and amounts used as well as other conditions and details are not to be construed in a matter that would unduly limit the scope of this invention.

Mice were immunized via subcutaneous injection with 500 ug ovalbumin protein alone (formulated as an aqueous solution in phosphate buffered saline) or mixed with 200 ug of one of the following IRMs:

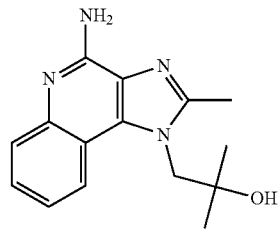

IRM 1

Prepared as a non-depot preparation, formulated to deliver 200 ug as an aqueous solution in an acetate buffered saline mixture containing cyclodextrin.

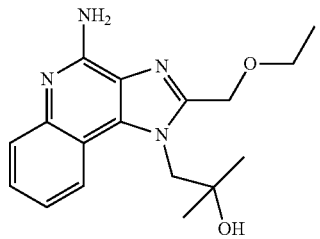

IRM 2

Prepared as a non-depot preparation, formulated to deliver 200 ug as an aqueous solution in a acetate buffered saline mixture containing cyclodextrin.

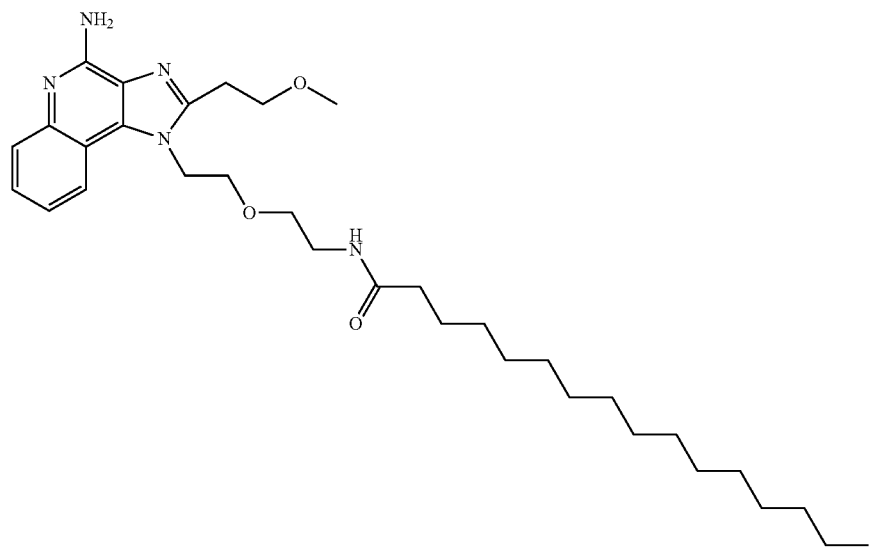

(lipidated IRM)

IRM 3 is a lipidated IRM. IRM 3 was formulated to deliver 200 ug using a depot preparation formulated as a micropartical precipitate (ppt), colloidal suspension, or as a micellar suspension. The precipitate composition was a microparticle (>1 micron, around 10-500 microns) composition formed by simply injecting IRM 3 dissolved in an organic solvent into an aqueous solution without surfactants. The resulting particle size range was broad, unlike the colloidal suspension (which provided a more monomodal submicron size). To form the colloidal formulation, IRM 3 was first dissolved in an organic and water miscible solvent (e.g. N-methyl pyrrolidone, DMSO, Cremophore EL), then added to an aqueous solution containing an appropriate amount of Tween 80. This causes the lipophilic IRM 3 to precipitate into colloidal particles, coated or surrounded by Tween 80 molecules, which act to prevent or minimize flocculation or agglomeration of the IRM particles. The higher the concentration of Tween 80, the finer the IRM colloidal particle size will be. At a concentration of Tween 80 greater than 2%, the IRM colloidal suspension turned into a translucent, almost clear solution, suggestive of a micellar encapsulation of the IRM by Tween 80. In this approach, the IRM may also partition between the inside of the micelle or be embedded in the micelle shell itself, contributing to its stability.

IRM 4 is known as CpG 1826 and was formulated to deliver 200 ug as an aqueous solution in phosphate buffered saline.

In each of the above cases, mice were injected subcutaneously 100 ul of formulation containing 200 ug of IRM and 500 ug of ovalbumin, then boosted 2 weeks later with same formulation. Five days after the boost, the spleens were removed and the cells stained with CD8, CD44, B220 and Kb-SIINFEKL tetramer.

The results are shown in FIG. 1. The data shown was gated on all live, CD8+, B220− events. The numbers in the upper right quadrants indicate the percent tetramer staining cells (antigen specific cells) out of total CD8+ T cells. The lipidated IRM molecule provides a clearly enhanced immune response than the non lipidated molecules. It is believed that this is due to both the lipid-modified nature of the compound, and the precipitate, colloidal suspension, and micellar suspension compositions, causing the IRM to remain resident within the localized tissue region for an extended period.

The complete disclosures of the patents, patent documents and publications cited herein are incorporated by reference in their entirety as if each were individually incorporated. In case of conflict, the present specification, including definitions, shall control. Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. A method of enhancing a subject's immune response, the method comprising:

depositing within a localized tissue region of the subject an immune response modifier (IRM) depot preparation that provides an extended residence time within the localized tissue region, wherein the IRM comprises an IRM portion of the formula 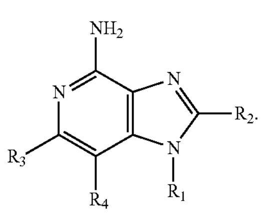 and having IRM activity; and a portion having antigenic activity that comprises:

an antigenic portion, or a solid support to which the antigenic moiety is paired;

wherein the immune response modifier portion is covalently coupled to the portion having antigenic activity through $R_1$;

wherein the immune response modifier portion comprises an imidazoquinoloine amine; a tetrahydroimidazolequinoline amine; an imidazopyridine amine; an imidazonapthyridine amine; or a tetrahydroimidazonaphihydine amine;

wherein the antigenic portion or antigenic moiety comprises a polypeptide, a polynucleotide, or a lipopolysaccharide;

wherein:

$R_1$ is a linker group;

$R_2$ is selected from the group consisting of:

-hydrogen;
-alkyl;
-alkenyl;
-aryl;
-substituted aryl;
-heteroaryl;
-substituted heteroaryl;
-alkyl-O-alkyl;
-alkyl-S-alkyl;
-alkyl-O-aryl;
-alkyl-S-aryl:
-alkyl-O-alkenyl;
-alkyl-S-alkenyl; and
-alkyl or alkenyl substituted by one or more substituents selected from the group consisting of:

—OH;
-halogen;
—$N(R_5)_2$;
—CO—$N(R_5)_2$;
—CS—$N(R_5)_2$;
—$SO_2$—$N(R_5)_2$;
—$NR_5$—CO—$C_{1-10}$alkyl;
—$NR_5$—CS—$C_{1-10}$alkyl;
—$NR_5$—$SO_2$—$C_{1-10}$alkyl;
—CO—$C_{1-10}$alkyl;
—CO—O—$C_{1-10}$alkyl;
—$N_3$;
-aryl;
-substituted aryl;
-heteroaryl;
-substituted heteroaryl;
-heterocyclyl;
-substituted heterocyclyl;
—CO-aryl;
—CO-(substituted aryl);
—CO-heteroaryl; and
—CO-(substituted heteroaryl);

$R_3$ and $R_4$ are each independently:

-hydrogen;
-halogen;
-alkyl;
-alkenyl;
—O-alkyl;
—S-alkyl; and
—$N(R_5)_2$;

or when taken together, $R_3$ and $R_4$ form a fused aryl or heteroaryl group that is optionally substituted by one or more substituents selected from the group consisting of;

-halogen;
-alkyl;

-alkenyl;
—O-alkyl;
—S-alkyl; and
—(R$_5$)$_2$;
or when taken together, R$_3$ and R$_4$ form a fused 5 to 7 membered saturated ring, optionally containing one or more heteroatoms and optionally substituted by one or more substituents selected from the group consisting of:
-halogen;
-alkyl;
-alkenyl,
—O-alkyl,
—S-alkyl, and
—N(R$_5$)$_2$, and
each R$_5$ is independently hydrogen or C$_{1-10}$alkyl.

2. The method of claim 1, wherein the localized tissue region comprises a breast cancer tumor, a stomach cancer tumor, a lung cancer tumor, a head or neck cancer tumor, a colorectal cancer tumor, a renal cell carcinoma tumor, a pancreatic cancer tumor, a basal cell carcinoma tumor, a cervical cancer tumor, a melanoma cancer tumor, a prostate cancer tumor, ovarian cancer tumor, or a bladder cancer tumor.

3. The method of claim 1, further comprising depositing a vaccine antigen within the localized tissue region.

4. The method of claim 3, wherein the vaccine antigen is not physically or chemically linked to the IRM.

5. The method of claim 3, wherein the subject's immune response to an antigen is enhanced, and wherein the antigen is an endogenous antigen.

6. The method of claim 1, wherein the IRM depot preparation comprises an IRM compound attached to support material.

7. The method of claim 1, wherein the IRM depot preparation comprises solid particles of IRM compound.

8. The method of claim 1, wherein the IRM depot preparation comprises an emulsion.

9. The method of claim 1, wherein the IRM depot preparation comprises micelles.

10. The method of claim 1, wherein the IRM depot preparation comprises IRM within a biodegradable polymer matrix.

11. The method of claim 1, wherein the IRM depot preparation comprises IRM compound incorporated into lipid membranes, lipid vesicles, or liposomes.

12. The method of claim 1, wherein the IRM depot preparation provides pulsed delivery of an IRM compound.

13. The method of claim 1, wherein the IRM depot preparation comprises an osmotically driven cylinder.

14. The method of claim 1, wherein the IRM depot preparation is delivered within the localized tissue region using needle injection.

15. The method of claim 1, wherein the IRM depot preparation is delivered within the localized tissue region using surgical implantation.

16. The method of claim 1, wherein the IRM depot preparation is delivered within the localized tissue region using laparoscopic implantation.

17. The method of claim 1, wherein the IRM depot preparation is delivered within the localized tissue region using catheter implantation.

18. The method of claim 1, wherein the IRM depot preparation is delivered within the localized tissue region using a microneedle array.

19. The method of claim 1, wherein the IRM depot preparation is delivered within the localized tissue region using high-velocity particle implantation.

20. The method of claim 1, wherein the IRM depot preparation is delivered within the localized tissue region using an image guiding technique selected from ultrasound, MRI, or real-time X-ray fluoroscopy.

* * * * *